US012702347B2

(12) United States Patent
Kane

(10) Patent No.: US 12,702,347 B2
(45) Date of Patent: Aug. 11, 2026

(54) METHOD AND APPARATUS FOR OUTPUTTING PREGNANCY MOVEMENTS

(71) Applicant: Zeinab Kane, London (GB)

(72) Inventor: Zeinab Kane, London (GB)

( * ) Notice: Subject to any disclaimer, the term of this patent is extended or adjusted under 35 U.S.C. 154(b) by 818 days.

(21) Appl. No.: 18/019,278

(22) PCT Filed: Jul. 30, 2021

(86) PCT No.: PCT/GB2021/051982
§ 371 (c)(1),
(2) Date: Feb. 2, 2023

(87) PCT Pub. No.: WO2022/029413
PCT Pub. Date: Feb. 10, 2022

(65) Prior Publication Data

US 2024/0008802 A1 Jan. 11, 2024

(30) Foreign Application Priority Data

Aug. 4, 2020 (GB) ..................................... 2012116

(51) Int. Cl.
*A61B 5/00* (2006.01)
*A61B 5/024* (2006.01)
(Continued)

(52) U.S. Cl.
CPC .......... *A61B 5/4343* (2013.01); *A61B 5/0011* (2013.01); *A61B 5/02411* (2013.01);
(Continued)

(58) Field of Classification Search
CPC . A61B 5/4343; A61B 5/0011; A61B 5/02411; A61B 5/1114; A61B 5/6823;
(Continued)

(56) References Cited

U.S. PATENT DOCUMENTS 4,898,179 A 2/1990 Sirota
5,913,834 A 6/1999 Francais
(Continued)

FOREIGN PATENT DOCUMENTS

CN 204147033 2/2015
CN 110123338 8/2019
(Continued)

OTHER PUBLICATIONS

International Search Report and the Written Opinion Dated Nov. 8, 2021 From the International Seaching Authority Re. Application No. PCT/GB2021/051982. (24 Pages).
(Continued)

*Primary Examiner* — May A Abouelela

(57) ABSTRACT

There is described a method of reproducing a movement occurring during a pregnancy, the method comprising: determining movement data relating to movements during pregnancy using a sensor device; transmitting the movement data from the sensor device to an external device; storing the movement data on the external device; and transmitting data relating to one or more movements of the movement data from the external device to an output device that is arranged to reproduce the movements, wherein said transmitting occurs substantially after the storing of the movement data; and reproducing the movements using the output device.

20 Claims, 6 Drawing Sheets

(51) Int. Cl.
*A61B 5/11* (2006.01)
*G09B 23/28* (2006.01)

(52) U.S. Cl.
CPC .......... *A61B 5/1114* (2013.01); *A61B 5/6823* (2013.01); *G09B 23/281* (2013.01)

(58) Field of Classification Search
CPC ....... A61B 5/1107; A61B 5/4356; A61B 7/00; A61B 5/4362; G09B 23/281
See application file for complete search history.

(56) References Cited

U.S. PATENT DOCUMENTS 6,135,969 A * 10/2000 Hale .................... A61B 5/4362 600/595
9,392,952 B1 * 7/2016 Oz ......................... A61B 5/349
10,898,097 B2 * 1/2021 Hayes-Gill ........... A61B 5/344
11,419,530 B2 * 8/2022 Ray ...................... A61B 5/4356
2006/0064040 A1 * 3/2006 Berger ................. A61B 5/4362 600/595
2010/0191154 A1 * 7/2010 Berger ............... A61B 5/02411 345/184
2010/0274145 A1 * 10/2010 Tupin, Jr. ............. A61B 5/0022 600/511
2011/0218413 A1 * 9/2011 Wang ................. A61B 5/02411 600/338
2012/0245490 A1 * 9/2012 Fausett ................. A61B 5/1114 600/595
2013/0096440 A1 * 4/2013 Kiraly .................... A61B 5/384 600/483
2013/0245436 A1 * 9/2013 Tupin, Jr. ............. A61B 5/6833 600/430
2014/0180169 A1 * 6/2014 Peters .................... A61B 5/391 600/588
2014/0249436 A1 * 9/2014 Kabakov .............. A61B 5/4362 600/509
2016/0058363 A1 * 3/2016 Hayes-Gill .......... A61B 5/4362 600/588
2016/0058429 A1 * 3/2016 Shinar .................. A61B 5/4809 600/551
2016/0157717 A1 * 6/2016 Gaster ................ A61B 5/02416 600/301
2016/0256132 A1 * 9/2016 Van De Laar ....... A61B 8/4416
2016/0270670 A1 * 9/2016 Oz ......................... A61B 5/352
2016/0270675 A1 * 9/2016 Oz ....................... A61B 5/6823
2016/0372009 A1 * 12/2016 Eggert .................... G16Z 99/00
2017/0127996 A1 * 5/2017 Hyde ....................... A61B 5/11
2017/0265799 A1 * 9/2017 Du ....................... A61B 5/0011
2017/0281087 A1 10/2017 Workman et al.
2018/0146868 A1 * 5/2018 Pon ........................ A61B 90/00
2018/0353121 A1 * 12/2018 Tian ..................... A61B 5/0053
2018/0353142 A1 * 12/2018 Shah .................... A61B 5/0022
2019/0254550 A1 * 8/2019 Divinsky ............. A61B 5/0006
2019/0269327 A1 * 9/2019 Singh ....................... A61B 8/56
2019/0320944 A1 * 10/2019 Vaidyanathan ...... A61B 5/7264
2020/0178880 A1 * 6/2020 Penders ............... A61B 5/7267
2020/0289047 A1 * 9/2020 Qi ........................ A61B 5/7278
2021/0236047 A1 * 8/2021 Yasutake .............. A61B 5/1126
2022/0047179 A1 * 2/2022 Omer ....................... A61B 5/25

FOREIGN PATENT DOCUMENTS

EP 1852058 11/2007
GB 2374716 10/2002
JP 2018-171265 11/2018

OTHER PUBLICATIONS

Patents Act 1977: Combined Search and Examination Report Under Sections 17 and 18(3) Dated Jan. 28, 2021 From the Intellectual Property Office of the United Kingdom of Great Britain Re. Application No. GB2012116.6. (10 Pages).
Patents Act 1977: Examination Report Under Section 18(3) Dated May 21, 2021 From the Intellectual Property Office of the United Kingdom of Great Britain Re. Application No. GB2012116.6. (4 Pages).
Huggies® “Huggies® Hug Belt”, Huggies®, 11 P., Feb. 16, 2017.
Communication Pursuant to Article 94(3) EPC Dated Feb. 16, 2026 From the European Patent Office Re. Application No. 21752126.9. (11 Pages).

* cited by examiner

METHOD AND APPARATUS FOR OUTPUTTING PREGNANCY MOVEMENTS

RELATED APPLICATIONS

This application is a National Phase of PCT Patent Application No. PCT/GB2021/051982 having International filing date of Jul. 30, 2021, which claims the benefit of priority of Great Britain Patent Application No. 2012116.6 filed on Aug. 4, 2020. The contents of the above applications are all incorporated by reference as if fully set forth herein in their entirety.

FIELD AND BACKGROUND OF THE INVENTION

The present disclosure relates to a method of outputting movements during pregnancy as well as related devices and systems.

When a person is pregnant, the people who are close to that person normally wish to be involved in the pregnancy. Often these people are particularly excited about feeling the foetus move or kick.

However, currently only the person that is pregnant is able to directly experience these movements. This can lead to disappointment for those other people with an interest in the pregnancy, such as fathers, those parents using surrogates, partners in same sex relationships, and more generally the friends and family of an expectant mother.

SUMMARY OF THE INVENTION

According to an aspect of the present disclosure, there is described a method of outputting a feature of movement data relating to movements during pregnancy, the method comprising: determining movement data using a sensor device; transmitting the movement data to an external device; storing the movement data on the external device; and outputting a feature of the movement data substantially after the storing of the movement data.

The method disclosed herein enables movement data to be stored for later playback or analysis, where this enables the movement data to be used by parties that are not in the proximity of the user at the time of any movements.

According to another aspect of the present disclosure, there is described a method of reproducing a movement occurring during a pregnancy, the method comprising: determining movement data relating to movements during pregnancy using a sensor device; transmitting the movement data from the sensor device to an external device; storing the movement data on the external device; and transmitting data relating to one or more movements of the movement data from the external device to an output device that is arranged to reproduce the movements, wherein said transmitting occurs substantially after the storing of the movement data; and reproducing the movements using the output device.

Preferably, the output device to which the data relating to one or more movements is transmitted, and/or to which the feature is output, is dependent on a property of the movement data.

The method of any preceding claim, wherein the output device to which the data relating to one or more movements is transmitted, and/or to which the feature is output, is dependent on an amount of access associated with one or more output devices.

Preferably, outputting a feature of the movement data comprises outputting the feature at least one minute after the storing of the movement data, preferably at least five minutes, more preferably at least thirty minutes, yet more preferably at least one hour, still more preferably at least six hours.

Preferably, outputting the feature comprises outputting a selected subset of the movement data.

Preferably, outputting the feature comprises reproducing a movement of the movement data.

Preferably, the reproduction depends on a user input. Preferably, the reproduction depends on a time period and/or a movement selected by a user.

Preferably, the outputting and/or the reproduction depends on a user and/or output device authorization.

Preferably, the outputting and/or the reproduction depends on a request from a user and/or an output device.

Preferably, the reproduction comprises reproducing at least one of: a movement force; a movement location; a movement direction; and a movement duration.

Preferably, determining movement data comprises detecting a movement that exceeds a threshold, preferably wherein the threshold comprises at least one of: a force threshold and a duration threshold.

Preferably, outputting the feature comprises presenting the movement data to a user, preferably presenting the feature on a user interface, more preferably presenting the feature on a user interface of the external device.

Preferably, outputting the feature comprises outputting the feature to multiple devices and/or users.

Preferably, determining the movement data comprises determining one or more of: a movement direction; a movement location; a movement force; and a movement duration.

Preferably, the feature comprises one or more of one or more of: a movement direction; a movement location; a movement force; a movement duration; a period of interest; one or more movements within the movement data; a peak in movement; a peak force; and a period of high movement.

Preferably, outputting a feature comprises outputting the movement data.

Preferably, the movement data relates to a plurality of movements.

Preferably, transmitting the movement data to an external device comprises transmitting the movement to a server and/or to a device arranged to process the movement data.

Preferably, the method further comprises processing the movement data to determine the feature. Preferably, processing the movement data comprises at least one of: identifying or selecting a period of interest; identifying or selecting one or more movements within the movement data; identifying a peak in movement; identifying a peak force; identifying a feature of the movement; identifying or selecting a period of high movement; filtering the movement data to remove noise and/or movements not caused by a foetus; and determining one or more parties to whom the movement data is to be transmitted.

Preferably, the processing occurs at the external device.

Preferably, the method further comprises outputting a notification following the transmission of the movement data to the external device and/or outputting a notification following the outputting of the feature. Preferably, outputting the notification comprises transmitting the notification to a further device.

Preferably, outputting the feature comprises transmitting the feature from the external device to an output device. Preferably, the output device is arranged to reproduce a movement of the movement data.

Preferably, the output device to which the feature is transmitted is dependent on a property of the movement data.

Preferably, the output device to which the feature is transmitted is dependent on a user selection, preferably a user selection by a pregnant party related to the movement data.

Preferably, the user selection occurs after the storage of the movement data.

Preferably, processing of the data is dependent on one or more of: the output device; a user of the output device; and a user selection.

Preferably, the sensor device is arranged to store a period of movement data prior to transmission to the external device.

Preferably, transmitting the movement data to the external device comprises transmitting movement data periodically and/or infrequently.

Preferably, the movement data is transmitted when a period of low movement is detected.

Preferably, the movement data is transmitted no more than: once every minute, once every hour, once every six hours, once every twelve hours, and/or once every twenty-four hours.

Preferably, the sensor device is arranged to enter a low power mode. Preferably, the sensor device is arranged to enter a low power mode during periods of low movement.

Preferably, the sensor device comprises a belt and/or a shell.

Preferably, the sensor device is arranged to be integrated with an item of clothing.

Preferably, the sensor device is arranged to be removably attached to an item of clothing.

Preferably, the movement data is transmitted using a wireless connection.

Preferably, the transmitting of the movement data and/or the outputting of the feature depends on the feature. Preferably, a device to which the movement data is transmitted and/or the device to which the feature is output depends on the feature.

Preferably, the method further comprises combining a plurality of movement data to provide a movement history. Preferably, the movement history relates to movement data for at least one day, at least one week, at least one month, and/or at least six months.

Preferably, the method further comprises combining the movement data with other data relating to a pregnancy. Preferably the other data comprises one or more of: a date of inception, and an expected date of birth.

Preferably, the transmitting of the movement data and/or the outputting of the feature is dependent on a user.

Preferably, the user is a pregnant party providing the movement data. Preferably, processing the movement data comprises determining a distribution list and/or access permissions relating to the movement data.

Preferably, the user is a party receiving the movement data.

Preferably, the method comprises monitoring a heartbeat using the sensor device.

Preferably, the method comprises outputting and/or reproducing the heartbeat.

Preferably, the method further comprises receiving further information relating to the pregnancy. Preferably, the further information comprises one or more of: a progress of the pregnancy, an approximate date of inception, an expected date of delivery, an experience of a pregnant party, and medical information relating to a pregnant party.

According to another aspect of the present disclosure, there is described a method of outputting movement data relating to movements during pregnancy, the method comprising: receiving movement data relating to movements during pregnancy; storing the movement data; and outputting the movement data substantially after the storing of the movement data.

According to another aspect of the present disclosure, there is described a method of reproducing movements during pregnancy, the method comprising: receiving movement data at an output device, wherein the movement data relates to one or more movements that have occurred substantially prior to the receipt of the movement data; and reproducing a movement of the movement data in dependence on a user input.

Preferably, the user input comprises one or more of: a selection of a movement period; a selection of one or more movements; and a selection of movements meeting a condition, such as a minimum force and/or duration.

Preferably, reproducing the movement comprises reproducing at least one of: a force of the movement; a location of the movement; a direction of the movement; and/or a duration of the movement.

Preferably, reproducing the movement comprises reproducing a component of a direction of a movement that is parallel to the stomach of a pregnant party and/or inverting before reproduction a component of a direction of a movement that is perpendicular to the stomach of the pregnant party.

Preferably, the method is a computer-implemented method.

According to another aspect of the present disclosure, there is described a sensor device for sensing movements during pregnancy, the sensor device comprising: a processor for determining movement data; a sensor element for recording the movement data; and a communication interface for transmitting the movement data to an external device.

Preferably, the device further comprises a power source. Preferably, the power source comprises a battery and/or an input arranged to receive power from a portable device.

Preferably, the device further comprises storage for storing the movement data. Preferably, the storage is arranged to store at least one minute of movement data, at least five minutes of movement data, at least thirty minutes of movement data, at least one hour of movement data, at least six hours of movement data, and/or at least twelve hours of movement data.

The device being capable of storing movement data enables the periodic transference of this movement data, which reduces battery consumption. Furthermore, this enables processing of a period of movement data by the device before transmission.

Preferably, the device further comprises an output element for reproducing a movement of the movement data in dependence on a user input.

Preferably, the communication interface comprises a wireless communication interface.

Preferably, the communication interface comprises a universal serial bus (USB) interface.

According to another aspect of the present disclosure, there is described a portable sensor device.

According to another aspect of the present disclosure, there is described a sensor device arranged to be attached to and/or integrated with an item of clothing.

According to another aspect of the present disclosure, there is described an output device for reproducing movements during pregnancy, the output device comprising: a communication interface for receiving movement data that has been determined substantially prior to the receipt by the communication interface; and an output element for reproducing a movement of the movement data.

According to another aspect of the present disclosure, there is described a portable output device.

According to another aspect of the present disclosure, there is described a device arranged to: receive, from a sensor device, movement data relating to movements during pregnancy; store the movement data; and output the a feature of the movement data substantially after the storing of the movement data.

Preferably, the device is arranged to process the movement data to determine the feature.

Preferably, outputting the feature comprises transmitting the feature to an output device arranged to reproduce a movement of the movement data.

According to another aspect of the present disclosure, there is described a system for outputting a feature of movement data relating to movements during pregnancy, the system comprising: a sensor device comprising: a processor for determining movement data; and a communication interface for transmitting the movement data to an external device; a storage device for storing the movement data; the external device; and an output device for outputting the movement data substantially after the storing of the movement data.

Optionally, a/the storage device is integrated with the sensor device.

Optionally, a/the storage device is integrated with the external device.

Preferably, the output device is integrated with the external device.

Preferably, the output device is arranged to reproduce a movement of the movement data, preferably wherein the output device is arranged to receive the movement from the external device.

Preferably, the output device comprises: a communication interface for receiving movement data; and a mechanism for reproducing a movement of the movement data in dependence on a user input.

Preferably, the external device is arranged to process the movement data before the outputting of the movement data.

According to another aspect of the present disclosure, there is described a device arranged to: receive, from a sensor device, movement data relating to movements during pregnancy; store the movement data; and transmit, to an output device arranged to reproduce the movements, data relating to one or more movements of the movement data substantially after the storing of the movement data.

According to another aspect of the present disclosure, there is described a system for reproducing a movement occurring during a pregnancy, the system comprising: a sensor device comprising: a processor for determining movement data relating to movements during pregnancy; and a communication interface for transmitting the movement data to an external device; a storage device for storing the movement data; the external device; and an output device arranged to reproduce one or more movements of the movement data substantially after the storing of the movement data.

Any feature described as being carried out by an apparatus, an application, and a device may be carried out by any of an apparatus, an application, or a device. Where multiple apparatuses are described, each apparatus may be located on a single device.

Any feature in one aspect of the disclosure may be applied to other aspects of the invention, in any appropriate combination. In particular, method aspects may be applied to apparatus aspects, and vice versa.

Furthermore, features implemented in hardware may be implemented in software, and vice versa. Any reference to software and hardware features herein should be construed accordingly.

Any apparatus feature as described herein may also be provided as a method feature, and vice versa. As used herein, means plus function features may be expressed alternatively in terms of their corresponding structure, such as a suitably programmed processor and associated memory.

It should also be appreciated that particular combinations of the various features described and defined in any aspects of the disclosure can be implemented and/or supplied and/or used independently.

The disclosure also provides a computer program and a computer program product comprising software code adapted, when executed on a data processing apparatus, to perform any of the methods described herein, including any or all of their component steps.

The disclosure also provides a computer program and a computer program product comprising software code which, when executed on a data processing apparatus, comprises any of the apparatus features described herein.

The disclosure also provides a computer program and a computer program product having an operating system which supports a computer program for carrying out any of the methods described herein and/or for embodying any of the apparatus features described herein.

The disclosure also provides a computer readable medium having stored thereon the computer program as aforesaid.

The disclosure also provides a signal carrying the computer program as aforesaid, and a method of transmitting such a signal.

The disclosure extends to methods and/or apparatus substantially as herein described with reference to the accompanying drawings.

The disclosure will now be described, by way of example, with reference to the accompanying drawings.

DESCRIPTION OF SPECIFIC EMBODIMENTS OF THE INVENTION

Figure 1:
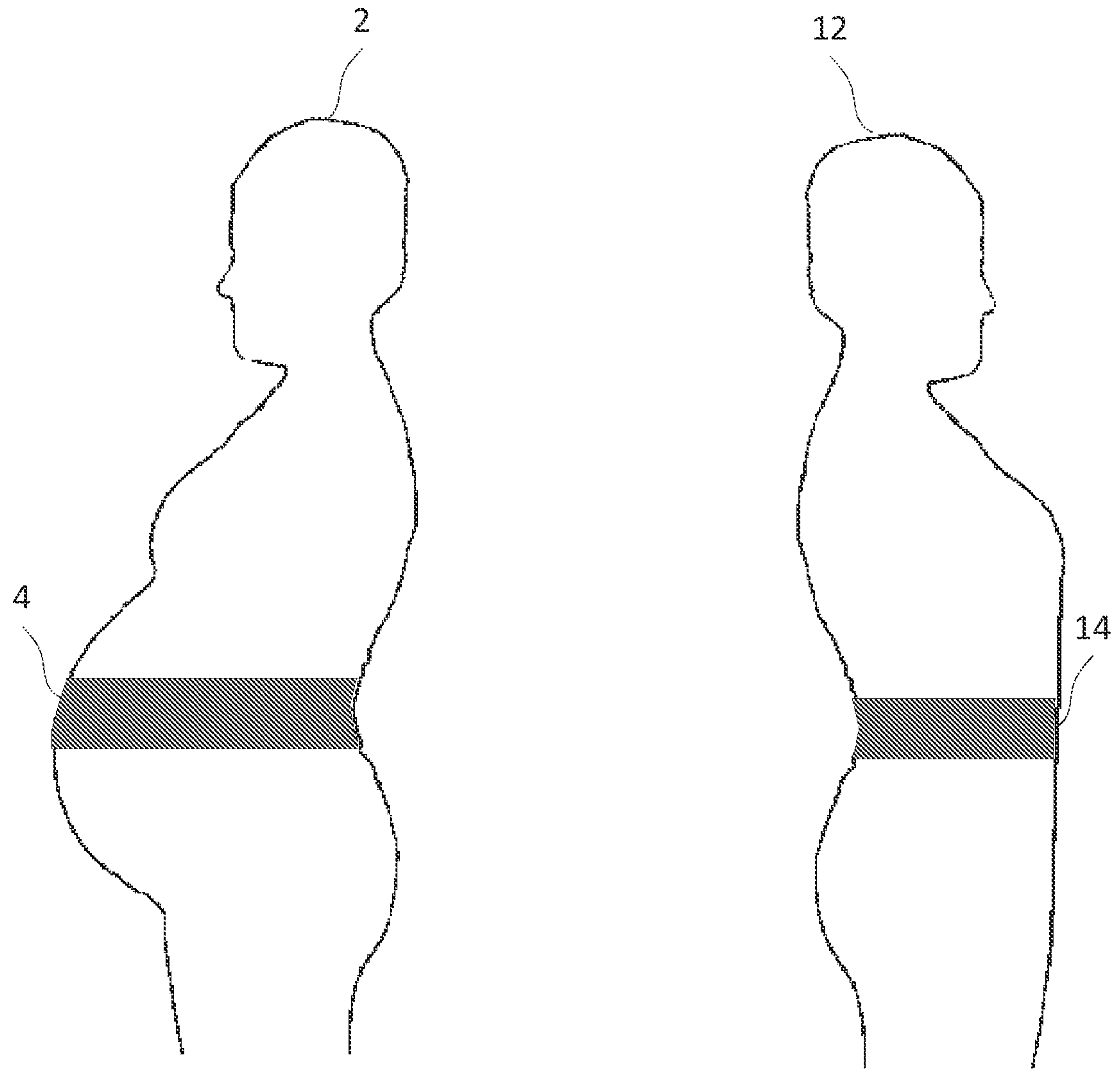
FIG. 1 shows a pregnant party wearing a pregnancy sensor device.

Referring to FIG. 1, there is shown a pregnant party 2 wearing a sensor device 4.

During the pregnancy of the pregnant party 2, the foetus moves inside the womb of the pregnant party. This movement can be felt by the pregnant party; in particular the pregnant party is able to feel the baby kicking.

A second party 12 that is close to the pregnant party 2, such as a partner, a family member, or a doctor, might wish to feel or study the movements of the foetus. Currently, this can be achieved by the second party placing their hand on the stomach of the pregnant party; however, this requires the second party to be nearby the pregnant party at the time of the movement. Furthermore, the movement felt by the second party is significantly different to the movement experienced by the pregnant party, not least since the sensations felt by a hand differ from those felt by the stomach.

The present disclosure relates to a sensor device for recording movements during a pregnancy, as well as a method of using this sensor device and methods and apparatuses for storing and reproducing the sensed movements. This enables a second party to experience the movements of a foetus in a similar way to the pregnant party.

Still referring to FIG. 1, the pregnant party 2 is able to record movements of the foetus using the sensor device 4, which in this embodiment comprises a belt. The movements detected by the sensor device are recorded and stored and these movements can subsequently be reproduced using a corresponding output device 14 that is placed on the stomach of the second party 12.

In the embodiment of FIG. 1, the sensor device 4 and the output device 14 each comprise a belt. It will be appreciated that more generally any device that comprises a movement sensor may be used. As examples, the sensor device may comprise one or more sensors placed on the stomach of the pregnant party 2, where these sensors may be held in place by an adhesive, or by friction. Yet more generally, the sensor device may comprise any device that is capable of detecting a movement of the stomach of the pregnant party, where this device need not necessarily be in contact with the stomach of the pregnant party. In some embodiments, the sensor device comprises a smartphone which may be placed in a pocket of the pregnant party and may sense movements from a distance; in these embodiments, the detection of movement is normally less accurate than in embodiments where sensors are in contact with the stomach.

In some embodiments, the sensor device 4 is arranged to be integrated with and/or attached to an item of clothing. For example, there may be provided a shirt or blouse containing sensors that are located near the stomach of the pregnant party 2. Similarly, there may be provided a garment, such as a belt, that comprises a pouch into which the sensor device can be placed. For example, there may be provided a garment comprising a pouch for a smartphone. This provides a cheap, straightforward, and comfortable way for the pregnant party to detect the movements of the foetus without needing to acquire and wear a substantial bulky device.

In some embodiments, the sensor device 4 is arranged to be attached to an item of clothing, for example the sensor device may comprise clips or adhesive that can be attached to a garment without causing substantial harm to that garment.

Typically, the sensor device 4 comprises an object that substantially covers the stomach of the pregnant party 2, for example the sensor device may comprise a shell-shaped object.

Similarly, the output device 14 typically comprises an object that substantially covers the stomach of the second party 12, such as a shell-shaped object.

An exemplary construction of the sensor device 4 comprises one or more of:

A fabric liner.

A printed circuit board (PCB) sensor device.

A fabric outer layer.

An exemplary construction of the output device 14 comprises one or more of:

A fabric liner.

A plurality of vibration motors. Specifically, the sensor device may comprise each of a plurality of high frequency vibration motors and/or a plurality of low frequency vibration motors.

A low density foam.

A fabric outer layer.

In some embodiments, the sensor device 4 comprises a heart rate monitor, such as a doppler device. The heartbeat of the foetus is recorded by this heart rate monitor and can then be shown to the second party 12 and/or analysed by the second party or by a doctor. The heartbeat of the foetus may also be reproduced by the output device 14, where the magnitude of the recorded heartbeats may be amplified so that the second party is able to clearly feel the heartbeats.

Figure 2:
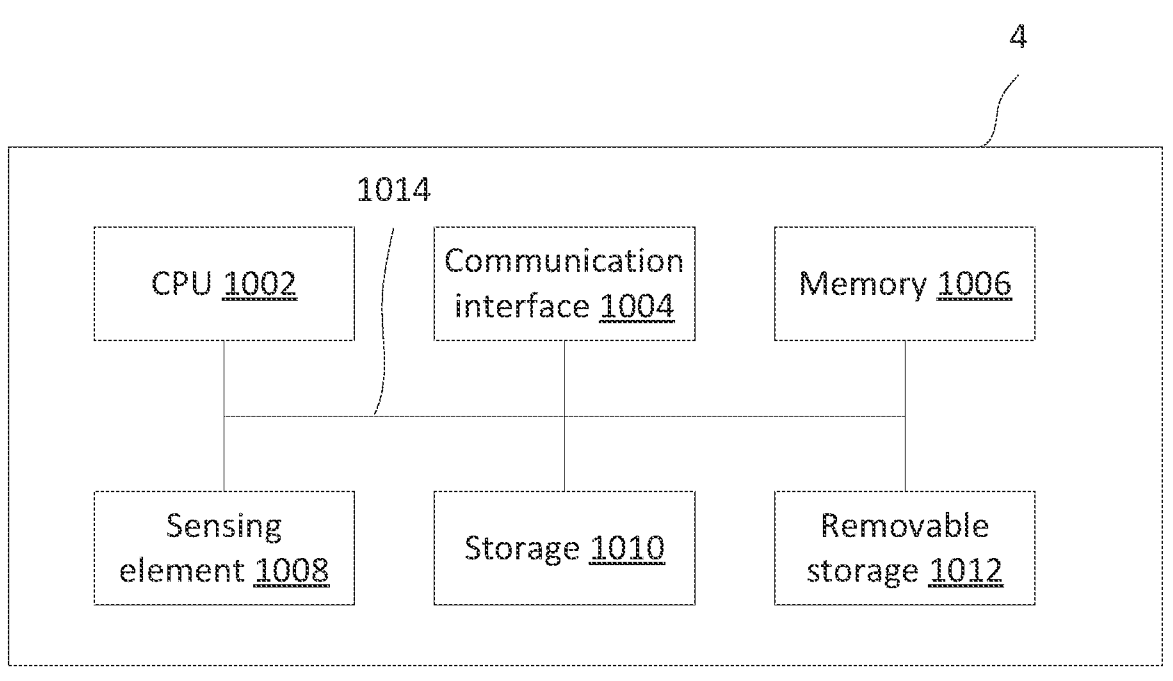
FIG. 2 shows a device on which the sensor device can be implemented.

Referring to FIG. 2, there is shown an exemplary sensor device 4 that comprises one or more sensing elements.

Specifically, the sensor device 4 of FIG. 2 comprises a processor in the form of a CPU 1002, a communication interface 1004, a sensing element 1006, a memory 1008, storage 1010, and a removable storage 1012, where the components are connected by a bus 1014.

The CPU 1002 executes instructions, including instructions stored in the memory 1006 and the storage 1008 of the sensor device 4.

The communication interface 1004 enables the sensor device 4 to communicate with other devices. The communication interface may comprise an area network interface or an Ethernet interface. More generally the communication interface may comprise any interface that enables communication, such as a Bluetooth® interface, an infrared interface, or a near field communication (NFC) interface. The communication interface may comprise a wireless interface or a wired interface.

The memory 1006 stores instructions and other information for use by the CPU 1002. Typically, the memory comprises both Random Access Memory (RAM) and Read Only Memory (ROM).

The sensing element 1008 comprises one or more elements arranged to detect a movement of the foetus in the womb of the pregnant party 2. The sensing element may comprise a single sensor or a plurality of sensors. Typically, the sensing element comprises an accelerometer. In various embodiments, the sensing element comprises one or more of: a pressure sensor, an acoustic sensor (e.g. a microphone), an optical sensor (e.g. a camera), and a gyroscope.

The storage 1010 provides mass storage for the user device 1000. Typically, the storage is in the form of a flash memory. It will be appreciated that other forms of memory such as hard disk drives and solid state drives may also be used for storage.

The removable storage 1012 provides a form of storage that enables simple transfer to other computer devices. The removable storage typically comprises an interface arranged to receive a universal serial bus (USB) drive or a memory card. This enables data that is recorded using the sensor device 4 to be transferred simply to a computer or to the output device 14.

The sensor device 4 further comprises a power supply (not shown), which may comprise a wired power supply (e.g. a connection to a mains power supply) and/or a wireless supply (e.g. a battery). Typically, the sensor device comprises a battery; this enables the pregnant party 2 to move freely while wearing the sensor device, which increases the user friendliness of the device and enables the recording of movement data in a wider range of situations. In some embodiments, the power supply is arranged to connect to a peripheral device, such as a smartphone; such a connection may use a USB connection. In practice, this enables the sensor device to be powered by a phone, which a user will typically keep on their person; this contributes to providing a portable sensor device.

In some embodiments, the sensor device 4 also comprises a user interface; the user interface is typically arranged to indicate when a recording is occurring, to enable the user to begin or end a recording, and/or to enable the user to set a threshold movement beyond which a recording begins. The user interface may comprise a display, a monitor, a mouse, and/or a keyboard.

Typically, the communication interface 1004 of the sensor device 4 is arranged to transfer information between the sensor device and a separate computer device, such as a personal computer or a server. This separate computer device is arranged to process the information and/or to control the sensor device. This transmission enables the data recorded by the sensor device to be reviewed on a more substantial user interface than is typically provided on the sensor device. The connected device is typically arranged to receive information from the sensor device in order to access data recorded taken by the sensing element 1008. In some embodiments, the communication interface is arranged to enable communication with a smartphone, so that an application on the smartphone can be used to control the sensor device.

The output device 14 is typically provided on a similar device as the sensor device 4 with the sensing element 1008 replaced by an output element (not shown). The output element is arranged to provide a movement that mimics a movement recorded by the sensing element. Typically, the output element comprises a mechanical output, such as a motor. The output device may also, or instead, comprise an audio output, such as a speaker, and/or a visual output such as a light. While the detailed description primarily considers the recording and reproduction of movements, more generally the disclosures herein are useable to recreate any sensation experienced by the pregnant party 2, such as sounds and sights.

The pregnant party 2 will feel the movement of the foetus internally and the sensor device 4 will therefore experience a force outwards from the stomach of the pregnant party. However, the output device 14 is attached to the exterior of the stomach of the second party 12 and so applies a force to the exterior of the stomach of the second party. In some embodiments, the output device is arranged to apply an outward force to the stomach of the second party, e.g. by using a pump to create a low pressure area above the stomach of the second party. In some embodiments, the output device is arranged to apply an inward force to the stomach of the second party, where the reproduction of the movement may still reproduce a location, a duration and a force of the movement. In such embodiments, the direction of the movement reproduced by the output device may be the inverse of the direction detected and recorded by the input device. Equally, the output device may reproduce the direction of a parallel component of a recorded movement and invert the direction of the recorded movement perpendicular to the stomach of the pregnant party.

In some embodiments, the sensor device 4 comprises an output element and/or the output device 14 comprises a sensing element. In other words, the sensor device and the output device may be provided in a single device. Combining the sensor device and the output device simplifies manufacture and enables a pair of users to obtain only a single device, where the pregnant party 2 wears this combined device for a period of time before passing it to the second party 12. Combining the sensor device and the output device also enables the pregnant party to quickly and easily replay movements of the foetus for their own benefit.

The manipulating, sharing, and analysis of recorded data may occur on the sensor device 14; typically, however, the recorded data is transmitted to an external device for review. In particular, the recorded data may be transferred to a remote device and/or a server, where it can be accessed using the internet.

In some embodiments, the recorded data is arranged to be accessed via an application such as a smartphone application (either directly from the sensing device or from a device to which the information is uploaded). This enables simple sharing of the recorded data between two parties as well as analysis and manipulation of the data as is further described below. With such an application, the pregnant party 2 is able to upload the recordings to the application, to highlight sections of the recorded data, e.g. to indicate the times of particularly strong movements to the second party 12, and to easily send the movement data to the second party.

Figure 3:
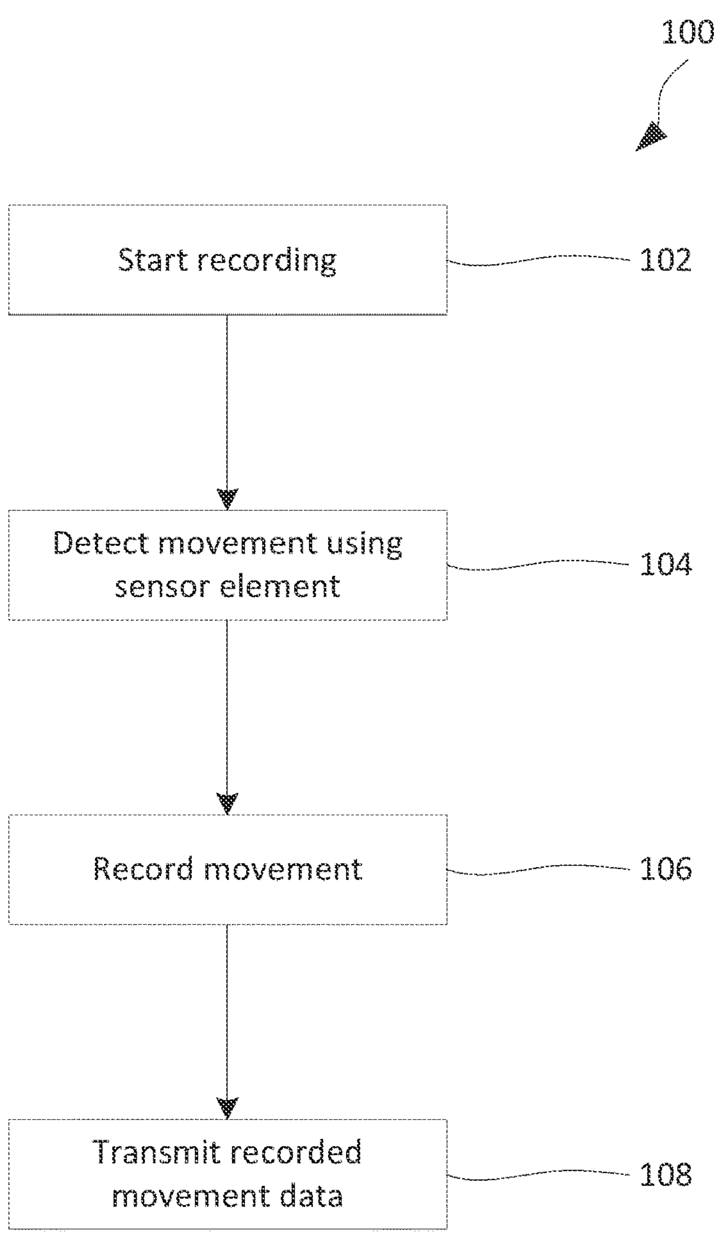
FIG. 3 shows a method of recording and outputting movements.

Referring to FIG. 3, there is shown a method 100 of recording movements and transmitting the recorded movements to another device.

In a first step 102, the sensor device 4 starts recording data relating to the movement of the foetus. Recording may begin based on an event, e.g. a movement above a certain threshold force or duration being detected, or may begin based on a user action, such as the pregnant party 2 placing the sensor on their stomach or the pregnant party pressing a 'start' button.

In a second step 104, the sensor device 4 detects one or more movements of the foetus using the sensing element 1008. This detection typically comprises detection of: a location of the movement(s), a force of the movement(s), a direction of the movement(s), and/or a duration of the movement(s).

In a third step 106, the movement(s) is recorded. This comprises the detected movement(s) being stored in the memory 1006, the storage 1010, and/or the removable storage 1012 of the sensor device 4.

In a fourth step 108, the recorded movement data is transmitted. Typically, this comprises transmitting the movement data to another device, such as a smartphone, a personal computer, and/or a server. The movement data may also be directly transmitted to the output device 14. Transmitting the data to an intermediary device beneficially enables the pregnant party 2 (or another party) to view the data relating to movements and to process this data before it is shared with the second party 12. This can also enable the pregnant party and/or the second party to choose periods of particular interest that they wish to reproduce.

In some embodiments, the movement data is transmitted to a plurality of other devices, where this enables multiple second parties to view the movement data.

Typically, the movement data is transmitted to a remote device using a wireless connection, but the data may also be shared to a local device via a wire or a removable connection interface. For example, the data may be output to a USB drive or a personal computer that is plugged into the sensor device.

While the movement data may be transmitted continuously, in some embodiments the movement data is transmitted periodically and/or infrequently, e.g. following an event such as a period of low movement. Periodic/infrequent sharing reduces battery consumption as well as the heating of the sensor device 4.

In some embodiments, movement data is shared no more than once every minute, no more than once every hour, no more than once every 6 hours, no more than once every 12 hours, or no more than once every 24 hours.

The sharing of the movement data with the output device 14 enables the movements to be reproduced by that output device as is described with reference to FIG. 4.

Figure 4:
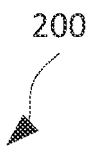
FIG. 4 shows a method of reproducing recorded movements.
Figure 4:
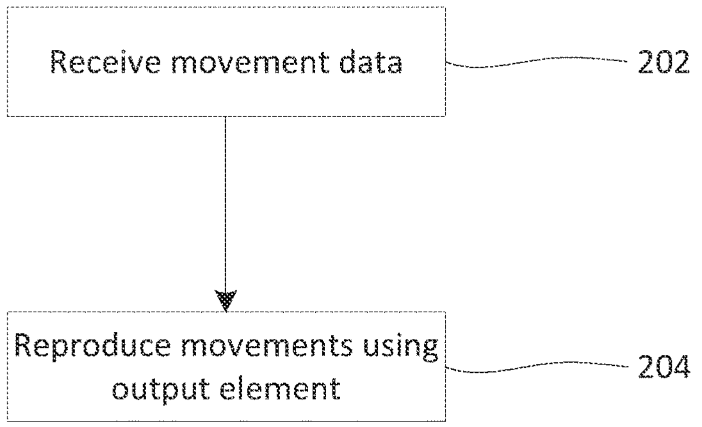

Referring to FIG. 4, a method 200 of reproducing recorded movements using the output device 14 is shown.

In a first step 202, the movement data is received by the output device 14; typically, this comprises receiving the data wirelessly from a server, e.g. via an application. This may also comprise receiving the data via a USB drive or a wired connection.

In a second step 204, the recorded movements defined by the movement data are reproduced. This comprises the output element of the output device 14 being used to reproduce the movements and typically comprises reproduce a location, force, direction and/or duration of each movement.

Typically, the reproduction of the recorded movement(s) occurs at a later time than the recording of the movement(s), where the reproduction of the movements is dependent on the second party 12 who is wearing the output device 14. For example, the second party is to select a period of time to reproduce and/or a specific set of movements to reproduce 'on-demand'. Similarly, the second party may be able to select movements to reproduce based on a feature of those movements; for example, the second part may choose to only reproduce movements over a certain force threshold or may choose only to reproduce periods of substantial movement.

In some embodiments, the output device 14 is arranged to receive and output the movements in substantially real-time; this can be achieved by the sensor device 4 and the output device communicating via a wired or wireless connection where data recorded by the sensor device is immediately transferred to the output device.

Figure 5:
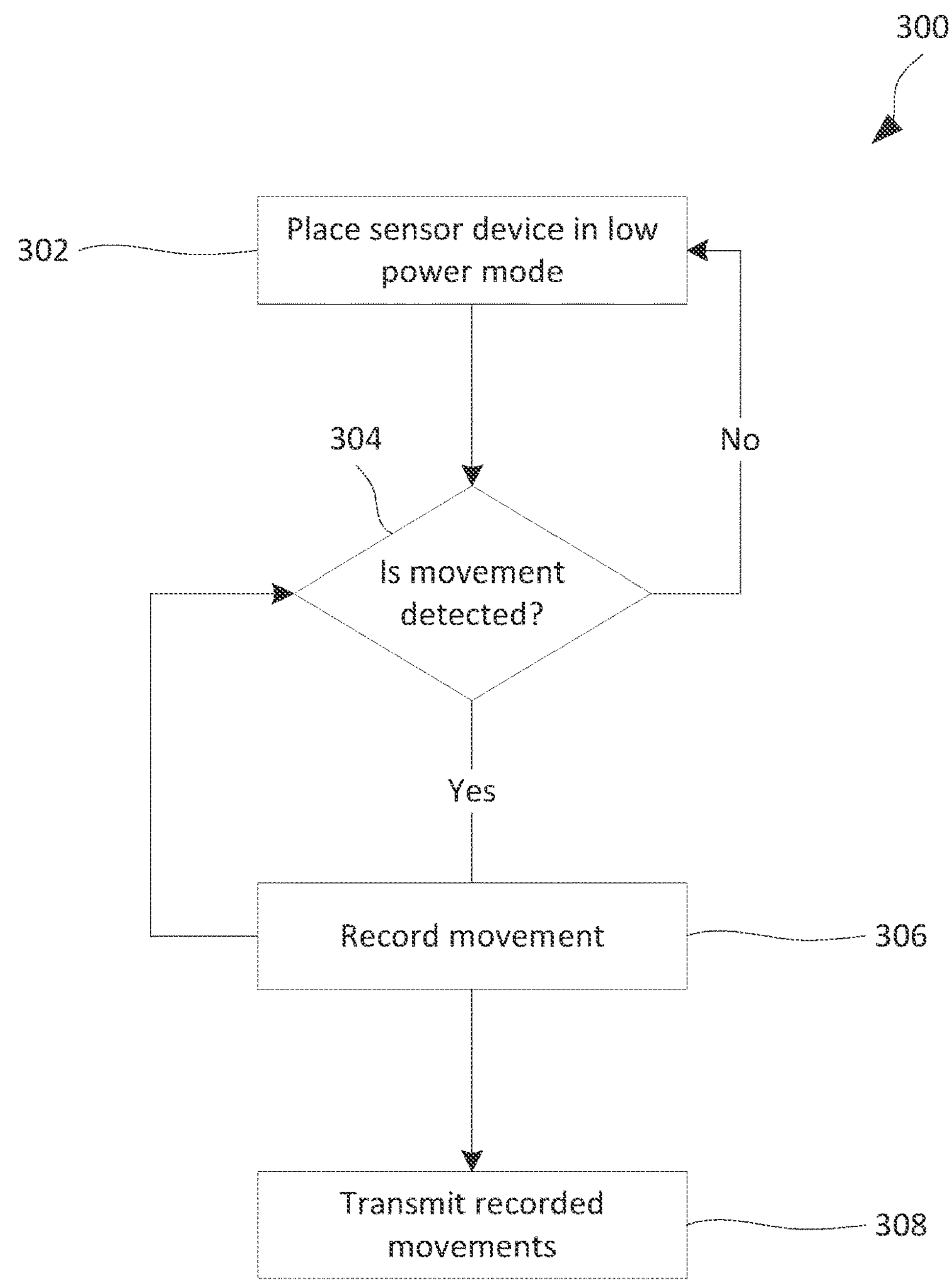
FIG. 5 shows a method of efficiently recording and outputting movements.

Referring to FIG. 5, there is shown a method 300 of efficiently recording movement data.

In a first step 302, the sensor device 4 is placed in a low power mode.

In a second step 304, the sensor device 4 determines whether a movement has occurred. The detection of movement typically requires a force threshold to be exceeded, where this threshold may be set by a user or may be determined automatically. In some embodiments, the threshold is determined based on previously recorded data; this enables the threshold to be based on the behavior of the foetus. The detection may also consider a duration threshold, a location determination, an evaluation of a direction of movement or an analysis of a movement profile. This detection step enables the sensor device to only record desired movements and to exclude movement unrelated to the foetus (e.g. a force on the sensors due the pregnant party placing something on her stomach). This reduces power consumption by reducing the amount of recorded measurements and also acts to filter the recorded data.

In a third step 306, the sensor device 4 records detected movements. The recording may consider a period before, during, and/or after the detected movement. In some embodiments, the storage 1010 and/or the removable storage 1012 of the sensor device comprises a buffer, where a historic period of movement is continuously stored. This ensures that data before the detection of a movement can be stored to ensure that no movements are missed and that the period preceding each movement is recorded.

Typically, the recording comprises recording a period surrounding each detected movement, where this period may be extended if more movement is detected before the end of the period. For example, the sensor device 4 may record movement data for at least 10 seconds before and/or after a detected movement, at least 30 seconds before and/or after a detected movement, and/or at least 60 seconds before and/or after a detected movement. This enables the second party 12 to experience a period including movements and quiet spells (as opposed to only recording movements).

At the end of a recording period, the sensor device 4 determines whether a movement has occurred. If no further movement has occurred, the device is returned to the low power mode.

This method enables recording of each movement that meets a threshold requirement without unnecessarily recording periods of low or no movement.

Features relating to each movement may also be determined and recorded so that the pregnant party 2 and the second party 12 can later identify the onset of a period of movement. Typically, the movements are recorded with reference to a time and date so that each party can later determine when the movements occurred. Other features that may be recorded include a peak force (during a recording period); the duration of a period of movements e.g. the length of a recording period); a movement density (an amount of movements during a recording period).

In a fourth step 308, the recorded movement data is transmitted to an external device. As with the method 100 of FIG. 3, this transmission may be periodic or infrequent or may be continuous. Typically, movements are output once a period of low movement is detected following a period of significant movement. Periodic or infrequent outputting reduces the power consumption and heating of the sensor device 4 so that the sensor device may be worn comfortably for an extended period of time.

The transmission of recorded movements may further comprise notifying the pregnant party 2 or the second party 12 of the movement, e.g. via a notification on an application. The notification may comprise a feature of the movement, e.g. a maximum force or a duration of movement.

Typically, the movement data is transmitted from the sensor device 4 to an external device, such as a server, that is arranged to process the movement data. This processing may comprise:

- Identifying features of the movement data, such as periods of substantial movement, and peak movement forces.
- Classifying each movement; this enables a party reviewing the movement data to rapidly view different types and strengths of movement (e.g. the second party 12 may wish to view how the force of the movement has increased as the foetus grows).
- Noise removal and/or the removal of movements not caused by the foetus.

Figures 6A, 6B:
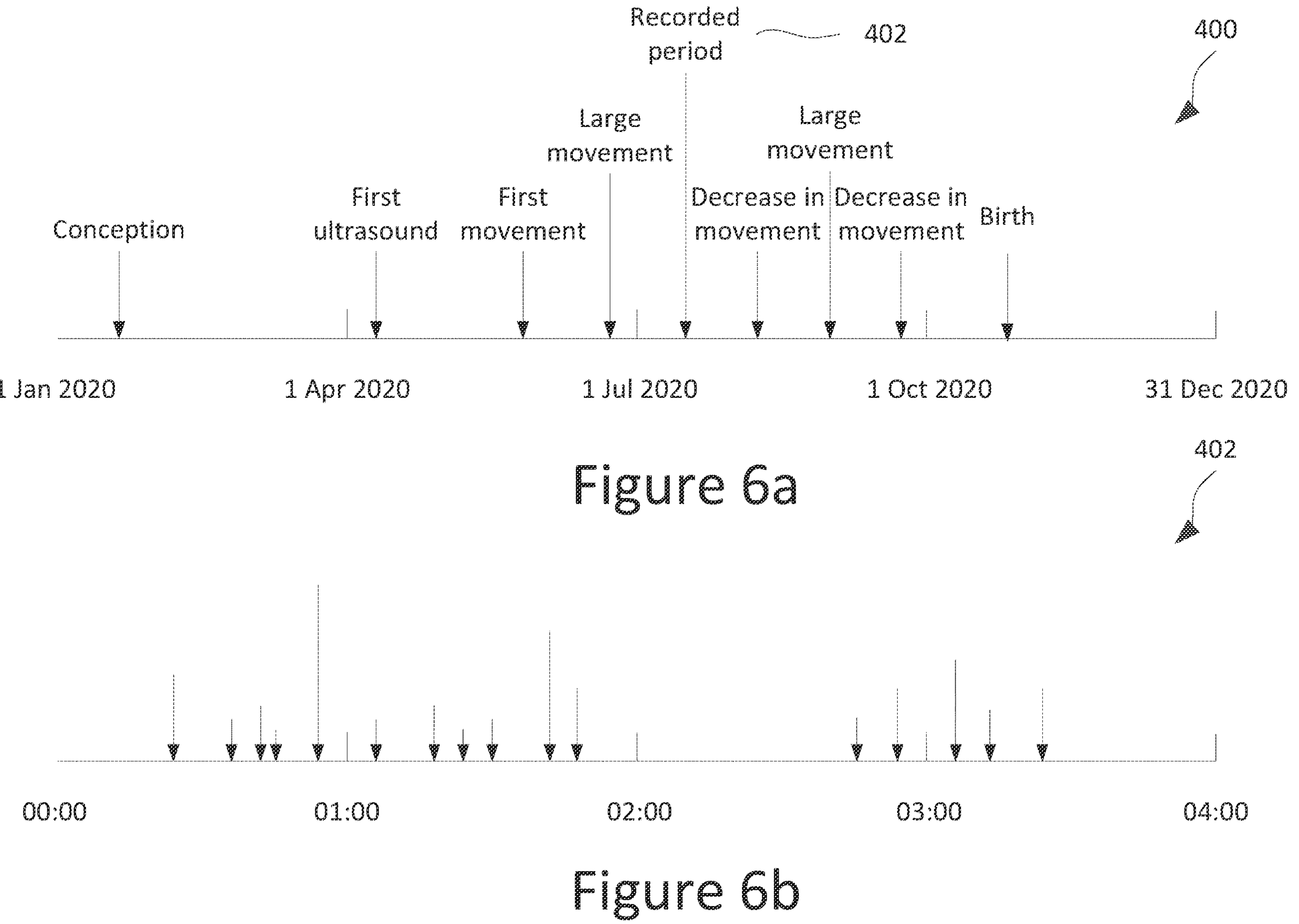
FIGS. 6*a* and 6*b* shows an interface for representing recorded movements.

Referring to FIG. 6, once the movement data has been transmitted, it is accessible by the pregnant party 2 and the second party 12. An exemplary method of representing the movement data is shown in FIGS. 6*a* and 6*b*.

Referring to FIG. 6*a*, there is shown a timeline of a pregnancy comprising a number of events. In particular, there is shown a date of conception, a date of a first ultrasound, the dates of various movements, and an expected or actual date of birth.

The present disclosure also considers the provision of an output that enables a party to view information relating to a pregnancy. Typically this output includes movement data; however, more generally, the information may include any data relating to the pregnancy, such as other substantial events. This enables the pregnant party 2 to see an overview of the pregnancy process and share this overview with interested parties. Each entry on the calendar of FIG. 6*a* may be linked to further information; for example, the calendar may be provided as part of an application and the party using this application may be able to click on the 'first ultrasound' entry to view photos of this ultrasound (with these photos typically being uploaded by the pregnant party).

As seen in FIG. 6*a*, large movements or other particularly significant movements (e.g. the first movement) may be labelled. This enables an interested party to rapidly identify and experience significant movements. Also recorded may be other points of interest, such as periods of decreased movement. In this way, the monitoring of the movement of the foetus may be used to track the pregnancy (movement tends to decrease towards the end of the pregnancy as the foetus runs out of space in the womb) and also to identify potentially problems. Where no substantial movement has been detected for a period of time, or where movement is detected in an unusual location, there may be a notification generated to alert the pregnant party 2 to a potential problem. Furthermore, the pregnant party 2 may be able to share the recorded movement data with a doctor to enable analysis of the data in the event of a problem occurring during the pregnancy.

FIG. 6*a* also shows a 'recorded period' 402; typically, there are a number of such recorded periods present on the timeline. A user is able to view information relating to the recorded periods in further detail, as shown in FIG. 6*b*.

The recorded period 402 shown in FIG. 6*b* comprises a series of movements, where the magnitude of each movement is shown. Typically, the user is able to select how a recorded period is shown, so that movements may be viewed with reference to other characteristic (e.g. a direction or a location). The user is then able to review features of the movements recorded by the sensor device 4. Furthermore, using the output device 14, the second party 12 is able to reproduce through these movements. The reproduction of the movements may be controlled much like a video player, where the second party 12 may be able to increase the playback speed, to skip to a desired time, or to scale the movements (e.g. proportionally increase the force of each movement).

Typically, the data is presented to a user using an interface that depends on that user; for example, the pregnant party 2 may have access to an interface that enables them to record their feelings, moods and experiences (e.g. the pregnant party may experience back pain). Similarly, the second party 12 may have access to an interface that provides information on how they might improve the situation of the pregnant party. This may involve the application automatically performing a web search following the recording of a situation by the pregnant party. Such a web search typically takes into account further information, such as a month of pregnancy, in order to provide helpful information to the second party.

More generally, the information that each party wishes to access may depend on that party; the pregnant party 2 and the second party 12 will typically be interested in different aspects of the pregnancy and of the movements and so will wish to view different information. To this end, the method of providing and transmitting movement data may comprise a configuration step where user preferences are recorded, e.g. using an application. The configuration step may comprise a party providing an input, such as a preference, an identification and/or an authorisation.

In some embodiments, the provision, transmission, and/or output of the movement data is dependent on an input from the pregnant party 2; in particular, the pregnant party is typically able to determine the amount of access that each party has. In practice, a spouse may have access to all of the recorded data whereas friends may only be shown milestone data, such as a first recorded movement.

The output of the movement data (e.g. the devices to which the movement data is output) may be dependent on any one or more of:

- A selection by a user (e.g. the pregnant party 2). This selection may be made before the recording of the movement data, so that the movement data may be automatically transmitted to an output device based on the pre-configured selection.
- An amount (or level) of access and/or an authorization of a user and/or an output device. In particular, the pregnant party 2 may be able to group users and/or output devices by amounts of access. In practice, a spouse may have access to all movement data, family may have access to a lesser amount of movement data and friends may have access to an even lesser amount. For example, friends may only be shown movements above a certain magnitude. The use of authorizations in this manner enables the pregnant party to control the dispersion of the movement data in order to improve privacy.
- A request by one or more users and/or output devices. For example, users may request to receive recent movements, where these requests may require approval from the pregnant party 2. In practice, this may comprise a device of a user making such a request, with or without the user's input—so a user's phone may send a request once the phone is turned on. This ensures that the pregnant party maintains control over the movement data.

In order to achieve this control by the pregnant party 2, the pregnant party (and/or another party) is typically able to make an account on an application, where data can then be shared with other parties by sharing between accounts or by sharing via an email or an instant message. Automatic sharing may be determined by the pregnant party so that certain parties are notified of the recording of movement data (and are able to access the movement data) as soon as this data is uploaded, other parties may only receive the movement data when the pregnant party manually sends this data.

Alternatives and Modifications

It will be understood that the present invention has been described above purely by way of example, and modifications of detail can be made within the scope of the invention.

While the detailed description has primarily considered the recorded movements being reproduced by the output device 14, it will be appreciated that the recorded movements may be used for other purposes, such as an analysis of the health of the foetus. As another example, the recorded data may be used to determine periods during which the foetus is particularly active and periods during which the foetus is sleeping. This may allow the pregnant party 2 and the second party 12 to plan certain activities accordingly. As an example, the second party may arrange to visit during a time when the foetus is normally active so that the second party can experience the movements in person.

Reference numerals appearing in the claims are by way of illustration only and shall have no limiting effect on the scope of the claims.

The invention claimed is:

1. A method of reproducing a movement occurring during a pregnancy, the method comprising:

determining movement data relating to movements of a fetus during pregnancy using a sensor device;

transmitting the movement data from the sensor device to an external device;

storing the movement data on the external device; and transmitting data relating to one or more movements of the movement data from the external device to an output device that is arranged to reproduce the movements;

wherein the external device is configured for transmitting the data relating to one or more movements to a plurality of output devices; and wherein the method comprises determining an output device to which to transmit the data in dependence on a property of the movement data.

2. The method of claim 1, wherein the output device to which the data relating to one or more movements is transmitted is dependent on an amount of access associated with the plurality of output devices.

3. The method of claim 1, wherein the transmitting data relating to one or more movements of the movement data comprises transmitting the data at least one minute after the storing of the movement data.

4. The method of claim 1, wherein the transmitting depends on one or more of:

a user input;

a time period and/or a movement selected by a user;

a user and/or output device authorization; and a request from a user and/or the output device.

5. The method of claim 1, comprising:

outputting the movement data to two or more of the plurality of output devices; and/or determining a distribution list relating to the movement data.

6. The method of claim 1, wherein determining movement data comprises detecting a movement that exceeds a threshold and/or wherein determining movement data comprises detecting a movement that exceeds at least one of: a force threshold and a duration threshold.

7. The method of claim 1, wherein the movement data comprises one or more of: a movement direction; a movement location; a movement force; a movement duration; a period of interest; one or more movements within the movement data; a peak in movement; a peak force; and a period of high movement.

8. The method of claim 1, further comprising one or more of:

processing the movement data to determine a feature of the movement data and/or to determine the movements;

identifying or selecting a period of interest;

identifying or selecting one or more movements within the movement data;

identifying a peak in movement;

identifying a peak force;

identifying or selecting a period of high movement;

filtering the movement data to remove noise and/or movements not caused by the fetus;

determining one or more parties to whom the movement data is to be transmitted; and processing the data at the external device.

9. The method of claim 1, wherein the sensor device is arranged to store at least one minute of movement data, at least five minutes of movement data, at least thirty minutes of movement data, at least one hour of movement data, at least six hours of movement data, and/or at least twelve hours of movement data.

10. The method of claim 1, further comprising outputting a notification following the transmission of the movement data to the external device.

11. The method of claim 1, wherein the output device is dependent on one or more of:

the property of the movement data; and a user selection by a pregnant party related to the movement data.

12. The method of claim 1, wherein:

the movement data is transmitted to the external device and/or the output device when a period of low movement is detected; and/or the movement data is transmitted to the external device no more than: once every minute, once every hour, once every six hours, once every twelve hours, and/or once every twenty-four hours; and/or the sensor device is arranged to enter a low power mode during periods of low movement.

13. The method of claim 1, comprising combining a plurality of movement data to provide a movement history, preferably wherein the movement history relates to movement data for at least one day, at least one week, at least one month, and/or at least six months.

14. The method of claim 1, wherein the sensor device is arranged to be integrated with and/or removably attached to an item of clothing and/or wherein the sensor device comprises a belt and/or a shell and/or wherein the sensor device is portable.

15. The method of claim 1, comprising:

monitoring a heartbeat using the sensor device; and/or outputting and/or reproducing the heartbeat monitored using the sensor device.

16. The method of claim 1, further comprising receiving and/or outputting further information relating to the pregnancy, wherein the further information comprises one or more of: a progress of the pregnancy, an approximate date of inception, an expected date of delivery, an experience of a pregnant party, and medical information relating to the pregnant party.

17. The method of claim 1, being a computer-implemented method.

18. The method of claim 1, comprising reproducing the movements using the output device.

19. A sensor device for sensing movements during pregnancy, the sensor device comprising:

a processor for determining movement data relating to movements of a fetus during pregnancy;

a sensor element for recording the movement data;

a storage for storing the movement data; and a communication interface for transmitting the movement data to an external device;

wherein the communication interface is configured for transmitting the data relating to one or more movements to a plurality of output devices; and wherein the output device to which the data relating to one or more movements is transmitted is dependent on a property of the movement data.

20. A system for reproducing a movement occurring during a pregnancy, the system comprising:

a sensor device comprising:

a processor for determining movement data relating to movements of a fetus during pregnancy; and a communication interface for transmitting the movement data to an external device;

a storage device for storing the movement data;

the external device; and a plurality of output devices arranged to reproduce one or more movements of the movement data substantially after the storing of the movement data;

wherein the external device is configured for transmitting the data relating to one or more movements to each of the plurality of output devices; and wherein the output device to which the data relating to one or more movements is transmitted is dependent on a property of the movement data.

* * * * *